(12) United States Patent
Morgan et al.

(10) Patent No.: US 6,391,875 B2
(45) Date of Patent: May 21, 2002

(54) PHARMACEUTICALLY ACTIVE MORPHOLINOL

(75) Inventors: Phillip Frederick Morgan, Apex; David Lee Musso, Raleigh; John Joseph Partridge, Chapel Hill, all of NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/886,391

(22) Filed: Jun. 22, 2001

Related U.S. Application Data

(63) Continuation of application No. 09/233,531, filed on Jan. 20, 1999, now Pat. No. 6,274,579.
(60) Provisional application No. 60/072,180, filed on Jan. 22, 1998.

(30) Foreign Application Priority Data

Jan. 21, 1998 (GB) .............................................. 9801230

(51) Int. Cl.$^7$ ............................................ A61K 31/535

(52) U.S. Cl. .................................... 514/238.8

(58) Field of Search ...................... 514/238.8

(56) References Cited

U.S. PATENT DOCUMENTS 5,648,347 A   7/1997  Mehta et al. ............ 514/231.2

FOREIGN PATENT DOCUMENTS

| EP | 0 170 430 A1 | 2/1986 |
| WO | 92/18489 | 10/1992 |
| WO | 01/62257 | 8/2001 |

OTHER PUBLICATIONS

Golden et al., "Bupropion in Depression," Arch. Gen Psychiatry, vol. 45, Feb. 1988.
Laizure, et al., "Pharmacokinetics of bupropion and its major basic metabolites in normal subjects after a single dose," Clin. Pharm. Ther., 1985 (38), pp. 586–589.
Suckow, et al., "Enantiomeric Determination of the Phenyl-morpholinol Metabolite of Buprorion in Human Plasma Using Coupled Achiral–Chiral Liquid Chromatography," Biomedical Chromatography, 1997, vol. 11, pp. 174–179.
Welch, et al., "Phmaracological significance of the species difference in bupropion metabolism," Xenobiotica, 1987, vol. 17, No. 3, pp. 287–298.
Suckow, et al., "Pharmacokinetics of Bupropion and Metabolites in Plasma and Brain of Rats, Mice, and Guinea Pigs," The American Society of Pharmacology and Experimental Therapeutics, 1986, vol. 14, No. 6, pp. 692–697.
Posner, J., et al., "The Disposition of Bupropion and Its Metabolites in Healthy Male Volunteers After and Multiple Doses," Eur. J. Clin. Pharmacol., 1985, vol. 29, pp. 97–103.

Ascher, J.A., et al., "Bupropion: A Review of its Mechanism of Antidepressant Activity," J. Cling. Psych., 1995, vol. 56, pp. 395–401.
Boswell, G. Evan, et al., "Synthesis and Anti–terrabenazine Activity of V–e Analogues of Dimethyl–2–phenylmorpholines," J. Heterocyclic Chem., vol. 33, pp. 33–39.
Boswell, G. Evan, et al., "Synthesis, Stereochemistry and Anti–Tetrabenazine Activity of Bicyclo Analogues 2–phenylmorpholines," J. Heterocyclic Chem., vol. 34, pp. 1813–1820.
Martin et al., "Antidepressant Profile of Bupripion and three Metabolites in Mice," Pharmacopsychiatry, 1990, vol. 23, pp. 187–194.
Eisman, et al., "The Isolation and Identification of Some Basic Urinary Metabolites of Bupropion–HCL in Man," Pharmacologist, 1979, vol. 21, p. 191.
Cooper et al., "Behavioral and Biochemical Effects of the Antidepressant, Bupropion (Wellbutrin): Evidence for Selective Blockade of Dopamine Uptake in Vivo," The Journal of Pharmacology and Experimental Therapeutics, 1980, vol. 215, No. 1.
Ferris et al., "Some Neurochemical Properties of a New Antidepressant, Bupropion Hydrochloride (Wellbutrin)," Drug Development Research, 1981, vol. 1, pp. 21–35.
Maxwell, et al., "Bupropion," Pharmacol & Biochem Propertics Drug Substances (M E Goldberg, Ed), Am Pharm Assoc. Pub., Washington, 1981, vol. 3, pp. 1–55.
Findlay, et al., "Pharmacokinetics of Bupropion, a Novel Antidepressant Agent, Following Oral Administration to Healthy Subjects," European Journal of Clinical Pharmacology, 1981, vol. 21, pp. 127–135.
Butz, et al., "Radioimmunoassay and Pharmacokinetic Profile of Bupropion in the Dog," The Journal of Pharmacology and Experimental Therapeutics, 1981, vol. 217, No. 3.
Ferris et al., "Bupropion: A New Antidepressant Drug, The Mechanism of Action of Which is Not associated with Down–Regulation of Postsynaptic β–Adrenergic, Serotonergic (5–HT$_2$), α2–Adrenergic, Imipramine and Dopaminergic Receptors in Brain," Neuropharmacology, 1983, vol. 22, No. 11, pp. 1257–1267.
Mehta, "The Chemistry of Bupropion, " J. Clinical Psychiatry, May 1983, 44:5 (Sec. 2).
Schroeder, David, "Metabolism and Kinetics of Bupropion," J. Clinical Psychiatry, May 1983, 44:5 (Sec. 2).

(List continued on next page.)

*Primary Examiner*—Dwayne C. Jones
(74) *Attorney, Agent, or Firm*—Bonnie L. Deppenbrock

(57) ABSTRACT

Disclosed is the compound (+)-(2S,3S)-2-(3-chlorophenyl)-3,5,5-trimethyl-2-morpholinol and pharmaceutically acceptable salts and solvates thereof, pharmaceutical compositions comprising them; also disclosed is a method of treating depression, attention deficit hyperactivity disorder (ADHD), obesity, migraine, pain, sexual dysfunction, Parkinson's disease, Alzheimer's disease, or addiction to cocaine or nicotine-containing (especially tobacco) products using such compound, salts, solvates or compositions.

1 Claim, 3 Drawing Sheets

OTHER PUBLICATIONS

Figure 1:
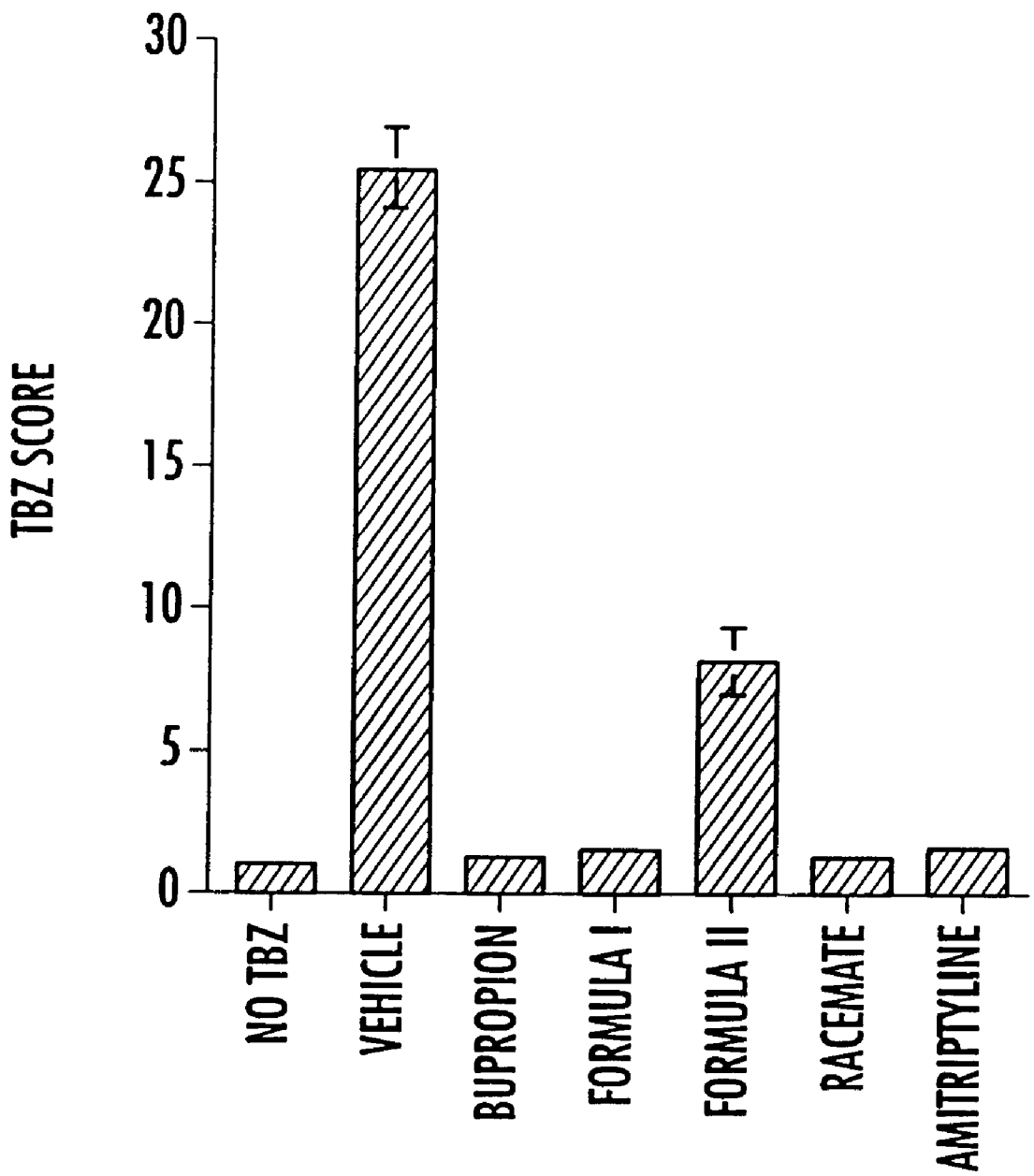

Lai, et al., "Clinical Pharmacokinetics of Bupropian: A Review," J. Clinical Psychiatry, May 1983, 44:5 (Sec. 2).

Cooper et al., "Determination of Bupropion and Its Major Basic Metabolites in Plasma by Liquid Chromatography with Dual–Wavelength Ultraviolet Detection," Journal of Pharmaceutical Sciences, Aug. 1984, vol. 73, No. 8.

Laizure et al., "Stability of Bupropion and its Major Metabolites in Human Plasma," Therapeuytic Drug Monitoring, 1985, vol. 7, pp. 447–450.

Cooper, et al., "Bupropion: Possible Rose of Major Metabolites in Mode of Action," Clin. Pharmacol. Ther., Feb. 1985, vol. 37, No. 2.

DeVane, et al., "The Effect of Experimentally–Induced Renal Failure on Accumulation of Bupropion and its major basic metabolites in plasma and brian of guinea pigs," Psychopharmacology, 1986, vol. 89, pp. 404–408.

Perumal, et al., "Effect of Plasma from Patients Contianing Bupropian and its Metabolites on the Uptake of Norepinephrine," Neuropharmacology, 1986, vol. 25, No. 22, pp. 199–202.

Thomas Smith et al., "Brain regional [$^3$H]flunitrazepam binding in rats chronically treated with bupropion or B.W.306U," Brain Research, 1986, 367, pp. 385–389.

Ferris et al., "Mechanism of Antidepressant Activity of Bupropion," J Clin Psychiatry Monograph, 1993, vol. 11, pp. 2–14.

Musso, et al., Synthesis and Evaluation of the Antidepressant Activity of the Enantiomers of Bupropion, Chirality, 1993, vol. 5, pp. 495–500.

Cooper, et al., "Evidence that the Acute Behavioral and Electrophysiolgical Effects of Bupropion (Wellbutrin) are Mediated by a Noradrenergic Mechanism," Neuropsychopharmacology, 1994, vol. 11, No. 2.

Modell, et al., "Comparative sexual side effects of bupropion, fluoxetine, paroxetine, and sertraline," Clinical Pharmacology & Therapeutics, 1996, vol. 61, No. 4.

Hsyu, et al., "Pharmacokinetics of Bupropion and its Metabolites in Cigarette Smokers versus Nonsmokers," J. Clin. Pharmacol., 1997, vol. 37, pp. 737–743.

PHARMACEUTICALLY ACTIVE MORPHOLINOL

This application is a continuation of Ser. No. 09/233,531 filed Jan. 20, 1999 now U.S. Pat. No. 6,274,579 which claims benefit of 60/072,180 Jan. 22, 1998.

This invention relates to an optically pure morpholinol, pharmaceutical formulations containing it and processes for their preparation and use.

BACKGROUND OF THE INVENTION

Bupropion hydrochloride, (±)-1-(3-chlorophenyl)-2-[(1,1-dimethylethyl)-amino]-1-propanone hydrochloride, is the active ingredient of Wellbutrin® which is marketed in the United States for the treatment of depression. It is also the active ingredient of Zyban® which is marketed in the United States as an aid to smoking cessation. Bupropion is a relatively weak inhibitor of the neuronal uptake of noradrenaline (NA), serotonin and dopamine (DA), and does not inhibit monoamine oxidase. While the mechanism of action of bupropion, as with other antidepressants, is unknown, it is presumed that this action is mediated by noradrenergic and/or dopaminergic mechanisms. Available evidence suggests that Wellbutrin® is a selective inhibitor of noradrenaline (NA) at doses that are predictive of antidepressant activity in animal models. See Ascher, J. A., et al, Bupropion: A Review of its Mechanism of Antidepressant Activity. *Journal of Clinical Psychiatry*, 56: p.395–401,1995.

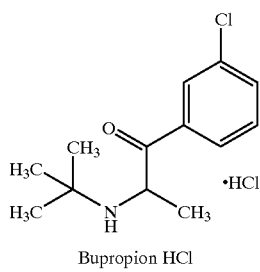

Bupropion HCl

Bupropion is extensively metabolized in man as well as laboratory animals. Urinary and plasma metabolites include biotransformation products formed via hydroxylation of the tert-butyl group and/or reduction of the carbonyl group of bupropion. Four basic metabolites have been identified. They are the erythro- and threo-amino alcohols of bupropion, the erythro-amino diol of bupropion, and a morpholinol metabolite. These metabolites of bupropion are pharmacologically active, but their potency and toxicity relative to bupropion have not been fully characterized. Because the plasma concentrations of the metabolites are higher than those of bupropion, they may be of clinical importance.

The morpholinol metabolite (+/−)-(2*,3*)-2-(3-chlorophenyl)-3,5,5-trimethyl-2-morpholinol hydrochloride is believed to be formed from hydroxylation of the tert-butyl group of bupropion.

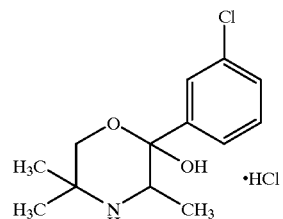

Morpholinol Metabolite of Bupropion HCl

SUMMARY OF THE INVENTION

It has now been discovered that despite the (−) form of the morpholinol metabolite predominating in human plasma samples, it is the (+) enantiomer, (+)-(2S, 3S)-2-(3chlorophenyl)-3,5,5-trimethyl-2-morpholinol in which the activity resides.

Thus the present invention provides, in one aspect, a compound of formula (I), (+)-(2S, 3S)-2-(3-chlorophenyl)-3,5,5-trimethyl-2-morpholinol or pharmaceutically acceptable salts and solvates thereof.

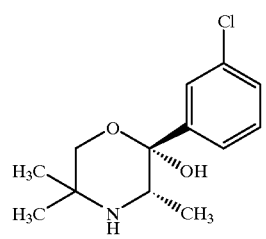

(I)

Another aspect of the invention is pharmaceutical compositions comprising a compound of formula (I) or pharmaceutically acceptable salts and solvates thereof together with one or more pharmaceutically acceptable carriers, diluents or excipients.

A further aspect of the present invention is the use of a compound of formula (I) or pharmaceutically acceptable salts and solvates thereof in therapy.

Yet another aspect of the invention provides methods of treating depression, attention deficit hyperactivity disorder (ADHD), obesity, migraine, pain, sexual dysfunction, Parkinson's disease, Alzheimer's disease, or addiction to cocaine or tobacco products in a human or animal subject comprising the administration to said subject of an effective amount of a compound of formula (I) or pharmaceutically acceptable salts and solvates thereof or pharmaceutical compositions thereof Yet another aspect of the present invention is the use of the compound of formula (I) or pharmaceutically acceptable salts and solvates thereof or pharmaceutical compositions thereof in the preparation of a medicament for the treatment of depression, attention deficit hyperactivity disorder (ADHD), obesity, migraine, pain, sexual dysfunction, Parkinson's disease, Alzheimer's disease, addiction to cocaine or tobacco products.

DESCRIPTION OF THE INVENTION

FIG. 1. Effect of Compounds at 25 mg/kg (ip) on TBZ-Induced Depression

Figure 2:
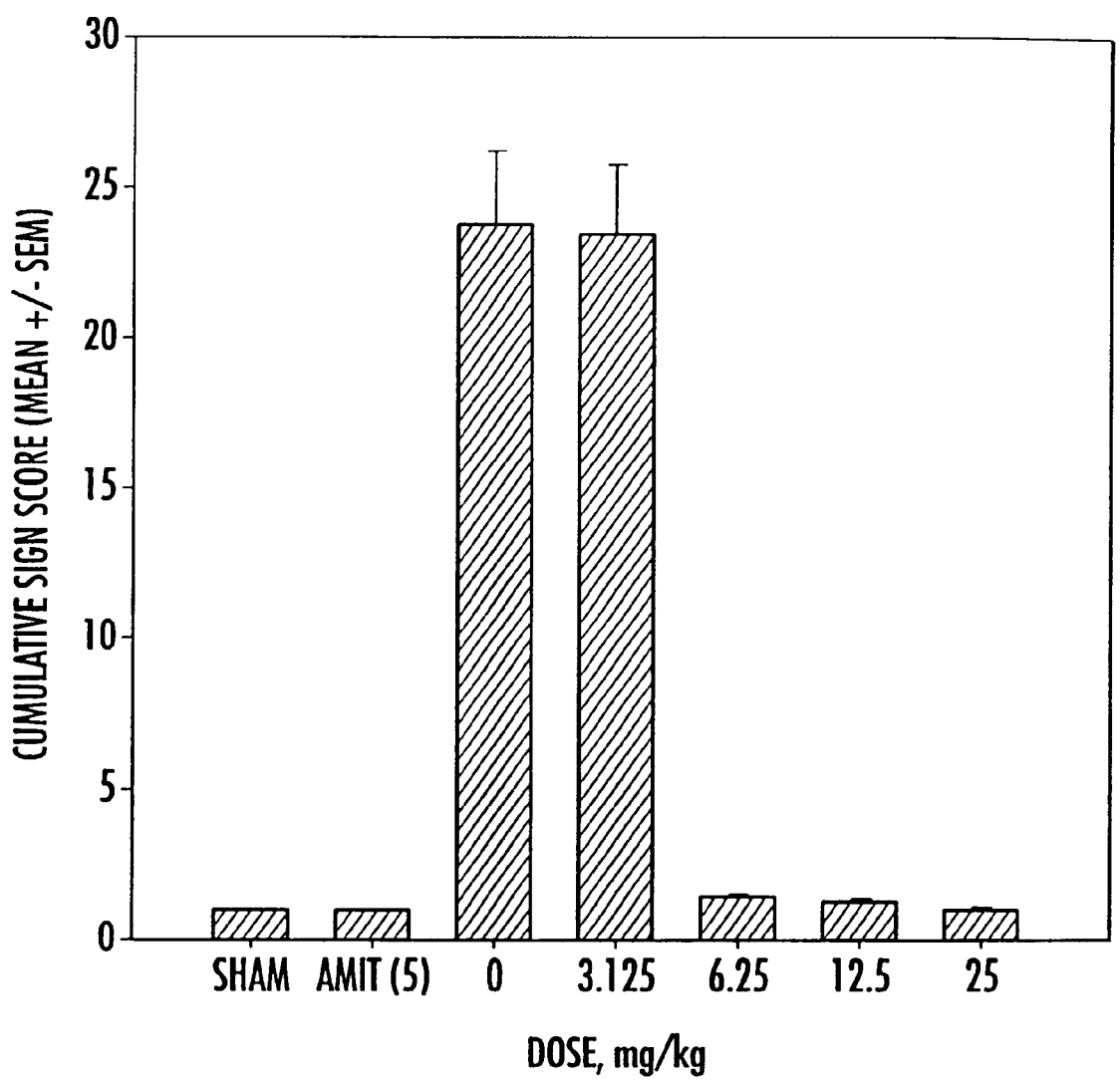

FIG. 2. Dose Response of Compound of Formula I Against TBZ-Induced Depression (Compounds administered 30 minutes prior to TBZ, Male, CD-1 Mice, i.p., n=6)

Figure 3:
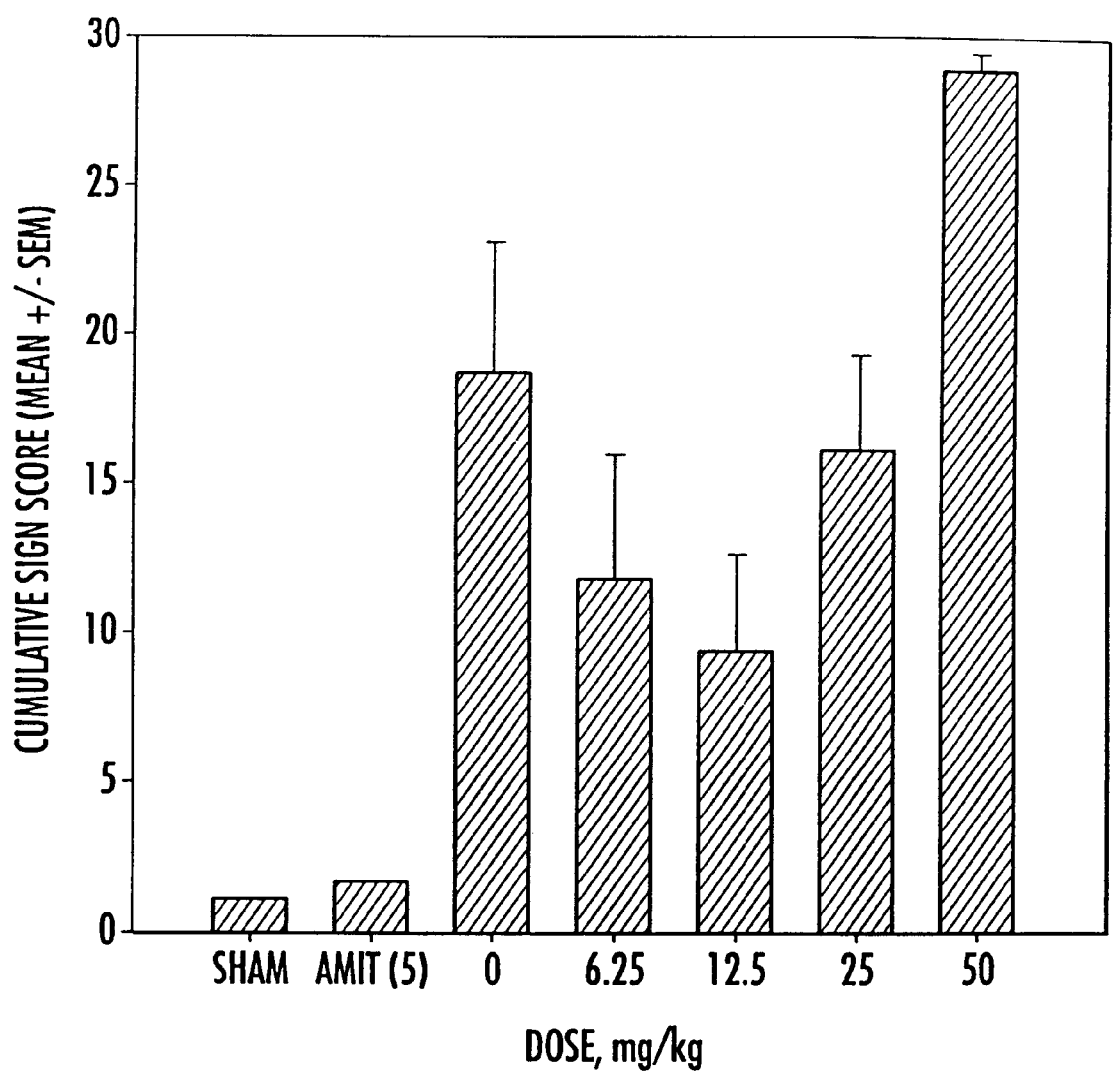

FIG. 3. Dose Response of Compound of Formula II Against TBZ-Induced Depression (Compounds administered 30 minutes prior to TBZ, Male, CD-1 Mice, i.p., n=6)

DETAILED DESCRIPTION OF THE INVENTION

The compound of formula (I) or pharmaceutically acceptable salts and solvates thereof may be prepared by first synthesizing the racemate of the morpholinol metabolite of bupropion and subsequently separating the (+) and (−) enantiomers of the racemate via HPLC.

The racemate of the morpholinol metabolite of bupropion hydrochloride ((+/−)-(2R*,3R*)-2-(3-chlorophenyl)-3,5,5-trimethyl-2-morpholinol hydrochloride) may be synthesized by the following process. To 3'-chloropropiophenone (10.0 g, 0.06 mol) in dioxane (50 mL) was added a solution of dioxane dibromide (14.9 g, 0.06 mol) in dioxane (50 mL). The reaction mixture was stirred for 2 h at ambient temperature and poured into a mixture of ice and water (500 mL). The mixture was extracted several times with methylene chloride. The combined extracts were dried ($Na_2SO_4$) and concentrated in vacuo to give 14.8 g (85%) of 2-bromo-3'-chloropropiophenone as a pale yellow oil. This was used without further purification. NMR (300 Mhz, $CDCl_3$); δ 7.99 (m, 1H), 7.90 (d, 1H), 7.57 (d, 1H), 7.44 (t, 1H), 5.22 (q, 1H), 1.91 (t, 3H).

To a solution of 2-bromo-3'-chloropropiophenone (19.3 g, 0.08 mol) in MeOH (100 mL) was added dropwise a solution of 2-amino-2-methyl-1-propanol (27.8 g, 0.31 mol) in methanol (200 mL) at ambient temperature. The mixture was stirred for 18 h and concentrated in vacuo. The residue was partitioned between water and diethyl ether. The combined organic phase was extracted with 10% aqueous hydrogen chloride. The combined aqueous acid extracts were chilled in an ice bath and made basic with 40% aqueous sodium hydroxide. The mixture was extracted with diethyl ether, the combined diethyl ether extracts were washed with water and saturated sodium chloride solution, dried ($K_2CO_3$) and concentrated in vacuo to give 15.0 g (75%) of (+/−)-(2R*,3R*)-2-(3-chlorophenyl)-3,5,5-trimethyl-2-morpholinol as an off-white solid.

(+/−)-(2R*,3R*)-2-(3-chlorophenyl)-3,5,5-trimethyl-2-morpholinol may be converted to (+/−)-(2R*,3R*)-2-(3-chlorophenyl)-3,5,5-trimethyl-2-morpholinol hydrochloride by the following process. A 6.0 g sample was dissolved in diethyl ether, chilled in an ice bath and ethereal hydrogen chloride added until the mixture was acidic. The resulting solid was filtered and recrystallized from ethanol/diethyl ether/ethereal hydrogen chloride mixtures to give 4.93 g of (+/−)-(2R*,3R*)-2-(3-chlorophenyl)-3,5,5-trimethyl-2-morpholinol hydrochloride as a white solid: m.p. 202–203° C. NMR (80 Mhz, DMSO-$d_6$); δ 10.9 (br, 1H), 8.85 (br, 1H), 7.60–7.41 (m, 5H), 4.04 (d, 1H), 3.50 (d, 1H), 3.37 (br s, 1H), 1.58 (s, 3H), 1.34 (s, 3H), 1.03 (d, 3H). Anal. Calcd for $C_{13}H_{19}Cl_2NO_2$: C, 53.43; H. 6.55; N, 4.79. Found: C, 53.54; H, 6.58; N, 4.75.

(+/−)-(2R*,3R*)-2-(3-chlorophenyl)-3,5,5-trimethyl-2-morpholinol hydrochloride may be converted back to its free base by the following process. A 3.0 g sample of (+/−)-(2R*,3R*)-2-3-chlorophenyl)-3,5,5-trimethyl-2-morpholinol hydrochloride was dissolved in water (100 mL) and diethyl ether was added (200 mL). The mixture was chilled in an ice bath and the pH was adjusted to >10 with 1.0N aqueous sodium hydroxide. After stirring for 30 min., the phases were separated and the aqueous phase was extracted with diethyl ether. The combined diethyl ether extracts were dried ($Na_2SO_4$) and concentrated in vacuo to give 2.6 g of (+/−)-(2R*,3R*)-2-(3-chlorophenyl)-3,5,5-trimethyl-2-morpholinol as a white solid. This was used without further purification for the chiral chromatography described below.

The (+) and (−) enantiomers of (+/−)-(2R*,3R*)-2-(3-chlorophenyl)-3,5,5-trimethyl-2-morpholinol may be separated by the following process. (+/−)-(2R*,3R*)-2-(3-chlorophenyl)-3,5,5-trimethyl-2-morpholinol (2.54 gms.) was dissolved in 250 ml of 2:8 Isopropyl alcohol:Hexane (both HPLC grade). A Daicel Chiralcel OD column (2×25 cm.) was equilibrated for one hour at 8 ml/min.in the elution solvent 1:9:0.2 Isopropanol:Hexane:Diethylanine. The solution of the (+/−)-(2R*,3R*)-2-(3-chlorophenyl)-3,5,5-trimethyl-2-morpholinol was injected in 1 ml. aliquots by an automated Waters Prep LC 2000, using a Waters 510 EF pump for injections. Each run was 15 minutes in length, using the conditions listed before. The separated optical isomers were collected by fraction collector (Waters) at a 2% above baseline threshold, based on 2 absorbance units full scale at 240 nm (Waters 490E UV detector). Each optical isomer solution was evaporated on a rotary evaporator at 40 degrees Centigrade and aspirator vacuum. After drying for 6 hours under high vacuum at room temperature, optical isomer 1 weighed 1.25 gm. and optical isomer 2 weighed 1.26 gm.

The enantiomeric purity of each isomer was assayed by analytical chiral HPLC on a Waters 860 HPLC with 996 Photodiode Array detector, using a Daicel Chiralcel OD-H column (4.6×250 mm.) eluted with 1:9:0.2 Isopropyl alcohol:Hexane: Diethylamine at 1 ml/min. Optical isomer 1 was 100% pure (RT. 6.117 min.). Optical isomer 2 was 99.19% pure (R.T. 6.800 min.), containing 0.81% optical isomer 1 (R.T. 6.133 min.).

Hydrochloride salts of the separated enantiomers were obtained by the following processes. 1.25 g (0.005 mol) of optical isomer 1 (retention time 6.117 min) ((−)-(2R,3R)-2-(3-chlorophenyl)-3,5,5-trimethyl-2-morpholinol) was dissolved in diethyl ether. The solution was filtered and the filtrate was chilled in an ice-bath adding ethereal hydrogen chloride until the solution was acidic. After standing at ambient temperature for 24 h, the resulting solid was filtered, washed with diethyl ether and dried in a vacuum oven at 60° C. for 18 h to give 1.32 g (90%) of (−)-(2R,3R)-2-(3-chlorophenyl)-3,5,5-trimethyl-2-morpholinol hydrochloride as a white solid: mp 208–209° C. NMR (300 Mhz, DMSO-$d_6$); δ 9.72 (br, 1H), 8.76 (br, 1H), 7.54–7.41 (m, 5H), 3.98 (d, 1H), 3.52 (d, 1H), 3.37 (br s, 1H), 1.53 (s, 3H), 1.29 (s, 3H), 0.97 (d, 3H). Anal. Calcd for $C_{13}H_{19}Cl_2NO_2$: C, 53.43; H, 6.55; N, 4.79. Found: C, 53.35; H, 6.57; N, 4.71. $[\alpha]_D^{20°\,C.}$=−33.2° (0.67, 95% EtOH).

1.26 g (0.005 mol) of optical isomer 2 (retention time 6.800 min) (+)-(2S,3S)-2-(3-chlorophenyl)-3,5,5-trimethyl-2-morpholinol) was dissolved in diethyl ether. The solution was filtered and the filtrate was chilled in an ice-bath adding ethereal hydrogen chloride until the solution was acidic. After standing at ambient temperature for 24 h, the resulting solid was filtered, washed with diethyl ether and dried in a vacuum oven at 60° C. for 18 h to give 1.36 g (93%) of (+)-(2S,3S)-2-(3-chlorophenyl)-3,5,5-trimethyl-2-morpholinol hydrochloride as a white solid: mp 208–2090° C. NMR (300 Mhz, DMSO-$d_6$); δ 9.87 (br, 1H), 8.76 (br, 1H), 7.54–7.41 (m, 5H), 3.99 (d, 1H), 3.51 (d, 1H), 3.37 (br s, 1H), 1.54 (s, 3H), 1.30 (s, 3H), 0.98 (d, 3H). Anal. Calcd for $C_{13}H_{19}Cl_2NO_2$: C, 53.43; H, 6.55; N, 4.79. Found: C, 53.51; H, 6.58; N, 4.73. $[\alpha]_D^{20°\,C.}$=+31.9° (0.64, 95% EtOH)

The absolute configuration of (+)-(2S,3S)-2-(3-chlorophenyl)-3,5,5-trimethyl-2-morpholinol was determined by the following x-ray crystallographic method. Crystal Data: $C_{13}H_{18}Cl_2NO_2$, M=291, Orthorhombic, space group $P2_12_12_1$, a=8.7348 (6), b=14.9824 (10), c=23.1605 (15) Å, V=3031 (4) Å$^3$, Z=8, Dc=1.276 Mgm$^{-3}$, F(000)=1226.95. Of 12224 reflections measured. 3764 were unique and 2318 which had I>3.0σ(I) were used in subsequent calculations. Data was collected on a Siemens SMART diffractometer using omega scans and monochromated MoKα radiation (λ=0.71073 Å). The positions of all non-hydrogen atoms were determined by direct methods and refined anisotropically. The hydrogen positions were all located in difference syntheses and included in subsequent refinement cycles using a riding model and an idealized bond length of 0.96 Å. The absolute configuration was determined by refinement of the Rogers' parameter and confirmed by an analysis of the 185 best Bijvoet intensity differences which indicated a probability of 0.006 that the model was in error. Least squares refinement minimized $\Sigma w(\Delta F)^2$ with weights based on counter statistics. The final agreement factors were $R_f$=0.064 (0.108 for all data), $R_w$=0.068 (0.081 for all data), and GoF=1.93. References included E. J. Gabe, Y. Le Page, J.-P. Charland, F. L. Lee and P. S. White, Journal of Applied Crystallography, 22, 384–387 (1989) and D. Rogers, Acta Crystallographica, A37, 734–741, 1981.

The amount of compound of formula (I) required to achieve the desired therapeutic effect will, of course depend on a number of factors, for example, the mode of administration, the recipient and the condition being treated. In general, the daily dose will be in the range of 0.02 to 5.0 mg/kg. More particular ranges include 0.02 to 2.5 mg/kg, 0.02 to 1.0 mg/kg, 0.02 to 0.25 mg/kg, 0.02 to 0.15 mg/kg and 0.02 to 0.07 mg/kg.

The compound of formula (I) may be employed in the treatment of depression, attention deficit hyperactivity disorder (ADHD), obesity, migraine, pain, sexual dysfunction, Parkison's disease, Alzheimer's disease, addiction to cocaine or tobacco products as the compound per se, but is preferably presented with one or more pharmaceutically acceptable carriers, diluents or excipients in the form of a pharmaceutical formulation The carriers, diluents and exipients must, of course, be acceptable in the sense of being compatible with the other ingredients of the formulation and must not be deleterious to the recipient. The carrier may be a solid or a liquid, or both, and is preferably formulated with the agent as a unit-dose formulation, for example, a tablet.

The formulations include those suitable for oral, rectal, topical, buccal (e.g. sub-lingual) and parenteral (e.g. subcutaneous, intramuscular, intradermal or intravenous) administration.

Formulations suitable for buccal (sub-lingual) administration include lozenges comprising a compound of formula (I) in a flavoured base, usually sucrose and acacia or tragacanth, and pastilles comprising the agent in an inert base such as gelatin and glycerin or sucrose and acacia.

Formulations of the present invention suitable for parenteral administration conveniently comprise sterile aqueous preparations of a compound of formula (I), preferably isotonic with the blood of the intended recipient. These preparations are preferably administered intravenously, although administration may also be effected by means of subcutaneous, intramuscular, or intradermal injection. Such preparations may conveniently be prepared by admixing the agent with water and rendering the resulting solution sterile and isotonic with the blood.

Formulations suitable for rectal administration are preferably presented as unit-dose suppositories. These may be prepared by admixing a compound of formula (I) with one or more conventional solid carriers, for example, cocoa butter, and then shaping the resulting mixture.

Formulations suitable for topical application to the skin preferably take the form of an ointment, cream, lotion, paste, gel, spray, transdermal patch, aerosol, or oil. Carriers which may be used include vaseline, lanolin, polyethylene glycols, alcohols, and combinations of two or more thereof.

It should be understood that in addition to the ingredients particularly mentioned above, the formulations may include other agents conventional in the art having regard to the type of formulation in question.

Biological activity of the compound of formula (I) was demonstrated by in vitro uptake models and the tetrabenazine-induced behavioural depression model. The racemic morpholinol metabolite, (+/−)-(2R*,3R*)-2-(3-chlorophenyl)-3,5,5-trimethyl-2-morpholinol, is referred to herein as "Racemate". The (−) form of the morpholinol metabolite is (−)-(2R, 3R)-2-(3-chlorophenyl)-3,5,5-trimethyl-2-morpholinol or pharmaceutically acceptable salts and solvates thereof and is referred to herein as a compound of formula (II):

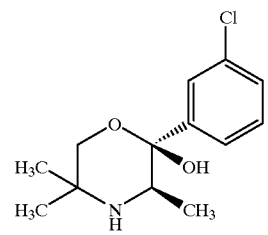

(II)

In vitro Synaptosomal Uptake Experiments. In vitro uptake was determined, as reported previously, using synaptosomes prepared from rat caudoputamen (for dopamine uptake) and hypothalamus (for NA and serotonin uptake) using [$^3$H]-dopamine, [$^3$H]-NA and [$^3$H]-serotonin as transport substrates, respectively. See Eckhardt, S. B., R. A. Maxwell, and R. M. Ferris, A Structure-Activity Study of the Transport Sites for the Hypothalamic and Striatal Catecholamine Uptake Systems. Similarities and differences. *Molecular Pharmacology*, 21: p. 374–9,1982.

Synaptosomes for use in obtaining in vitro uptake data were prepared from hypothalamus or striatum by gently homogenizing the tissue in a 0.3 M sucrose/25 mM Tris pH 7.4 buffer containing iproniazid phosphate to inhibit monoamine oxidase. The homogenate was centrifuged at 1100×g at 4° C. for 10 min and the supernatant was used for uptake studies. The supernatant (~1 mg tissue protein) was incubated with Km concentrations of [$^3$H]-noradrenaline, [$^3$H]-dopamine or [$^3$H]-serotonin at 37° C. for 5 minutes in Modified Krebs-Henseleit buffer (118 mM NaCl, 5 mM KCl, 25 mM $NaHCO_3$, 1.2 mM $NaH_2PO_4$, 1.2 mM $MgSO_4$, 11 mM Dextrose, 2.5 mM $CaCl_2$) in the absence and presence of drug. Under these conditions uptake was linear with respect to both for substrate and tissue (with <5% total substrate transported). Non-specific uptake was defined as uptake at 0° C. [$^3$H]-substrate, which had been transported into synaptosomes, was separated from free [$^3$H]-substrate by filtration over GF/B filters and washing with cold Krebs-Henseleit buffer. The filters were counted for tritum in a liquid scintillation spectrometer.

The data for in vitro synaptosomal uptake are presented as Table 1. Among the 2 enantiomers of the morpholinol metabolite of bupropion, the (+) enantiomer, the compound of formula (I), inhibited noradrenaline (NA) uptake with an $IC_{50}$ of 2.2 μM. In contrast, the (−) enantiomer was ineffective at a concentration of 30 μM. On dopamine (DA) uptake, the compound of formula (I) had an $IC_{50}$ of ~10 μM while the (−) enantiomer was inactive at 30 μM. Neither compound inhibited serotonin uptake at 30 mM.

For comparison, Wellbutrin® was equipotent for inhibiting DA and noradrenaline uptake with $IC_{50}$ values of 1.9 and 2.2 μM, and did not inhibit serotonin uptake at 30 μM. Imipramine (a non-specific tricyclic antidepressant) inhibited NA uptake and serotonin uptake with $IC_{50}$ values of 0.072 and 0.24 μM, respectively.

The compound of formula (I) was approximately twice as potent as Wellbutrin® as an NA inhibitor but, unlike the latter, was approximately 10-fold less potent as an inhibitor of dopamine uptake. These data are consistent with the observed noradrenergic actions of Wellbutrin® and the racemic morpholinol metabolite of bupropion, (+/−)-(2R*, 3R*)-2-(3-chlorophenyl)-3,5,5-trimethyl-2-morpholinol hydrochloride, (306U73) in vivo, at their respective anti-TBZ doses (Cooper, B. R., et al, *Neuropsychopharmacology*, 11: p. 133–41,1994). Behavioral and electrophysiological data suggest that the effects of Wellbutrin® are mediated by a noradrenergic mechanism (ibid).

Tetrabenazine-induced Behavioural Depression Experiments. Tetrabenazine (TBZ)-induced behavioural depression was used as an in vivo measure of antidepressant activity. The test has been validated with a wide range of antidepressants, known to act through noradrenergic mechanisms (Cooper B. R. et al, "Animal models used in the prediction of antidepressant effects in man", J. Clin. Psychiatry 44: 63–66, 1983). Moreover, the test was also used to identify Wellbutrin® as an anti-depressant. Briefly, animals were injected with the candidate agent (p.o. or i.p.) 30 minutes before receiving an i.p. injection of tetrabenazine (35 mg/kg, as the HCl salt—prepared fresh for each use). Assessments were performed 30 minutes thereafter and included: locomotor activity (1–4 scale); ptosis (1–4 scale) and body temperature as described previously (Cooper, B. R., J. L. Howard, and F. E. Soroko, Animal models used in prediction of antidepressant effects in man (*Journal of Clinical Psychiatry*, 44: p. 63–6,1983). In all studies, the scientist performing the assessments was blind to the treatments. All parameters were weighted equally to give a "lumped" score (X) through the following algorithm:

X=(1+Ptosis score)/(Activity score*[Temp,treated/Temp,control]

Results from the tetrabenazine-induced behavioural depression model are as follows. Assessed in vivo at 25 mg/kg (ip) the compound of formula (I), the racemate, Wellbutrin® and, for comparison, amitryptyline all abolished the tetrabenazine-induced behavioural depression. In contrast, the (−) enantiomer showed only modest activity FIG. 1).

In the TBZ model of behavioural depression, activity resided in the compound of formula (I). When analysed in a dose-effect study with TBZ, the activity showed a sharp increase in activity between 3 mg/kg and 6 mg/kg (ip) (FIG. 2). The compound of formula II, in comparison, did not possess dose-related activity and, at 50 mg/kg, appeared to worsen the animal's condition (FIG. 3). In FIGS. 2 and 3, AMIT (5) refers to amitryptiline dosed at 5 mg/kg and SHAM refers to a control group of animals that have recieved no medication at all.

Since the TBZ test has been predictive of anti-depressants acting through noradrenergic mechanisms and the compound of formula (I) is an inhibitor of noradrenaline uptake and Wellbutrin® is metabolised to this morpholinol in vivo, the data suggest that the anti-depressant activity of Wellbutrin® is likely to result from the effects of the compound of formula (I). (Welch, R. M., A. A. Lai, and D. H. Schroeder, Pharmacological significance of the species differences in bupropion metabolism. *Xenobiotica*, 17: p. 287–98,1987).

By extension, other activities of Wellbutrin® could be attributed to the compound of formula (I). In particular, a noradrenergic mechanism is common to molecular mechanism for Wellbutrin's effects on smoking cessation is less well understood, a catecholaminergic pathway is thought to participate in the behavioural reinforcing properties of nicotine. Wellbutrin® (and, by extension, the compound of formula (I)), by augmenting NA release into brain synapses, could mimic some of the actions of nicotine and, thus, decrease the signs associated with nicotine withdrawal. Additionally, amphetamines have been used to treat obesity. The addictive properties of amphetamine, however, preclude its use for most obese patients. Wellbutrin® causes weight loss and, like amphetamine, acts through a noradrenergic mechanism. (Zarrindast, M. R. and T. Hosseini-Nia, Anorectic and behavioural effects of bupropion. *General Pharmacology*, 19: p. 201–4,1988 and Harto-Truax, N., et al, Effects of Bupropion on Body Weight *Journal of Clinical Psychiatry*, 44: p. 183–6,1983). However, unlike amphetamine, Wellbutrin® is not addictive. (Lamb, R. J. and R. R. Griffiths, Self-administration in Baboons and the Discriminative Stimulus Effects in Rats of Bupropion, Nomifensine, Diclofensine and Imipramine. *Psychopharmacology*, 102: p. 183–90,1990; Bergman, J., et al., Effects of Cocaine and Related Drugs in Nonhuman Primates. III. Self-administration by Squirrel Monkeys. *Journal of Pharmacology & Experimental Therapeutics*, 251: p. 150–5,1989 and Johanson, C. E.; and J. E. Barrett, The Discriminative Stimulus Effects of Cocaine in Pigeons. *Journal of Pharmacology & Experimental Therapeutics*, 267: p. 1–8,1993). By extension, the compound of formula (I) would also be expected to have efficacy in obesity and cocaine addiction.

Safety and Toxicity. Additional dose-ranging studies were performed to determine the range of safe does for the isomers and the racemate. Animals were observed for the presence of serious adverse events (e.g. seizures and deaths) following administration of the compounds of formula I, formula II or the racemate by the oral and intraperitoneal (i.p.) routes. The data are presented as Table II.

Administered orally, at 100 mg/kg p.o., seizures were observed with the compound of formula II and the racemate but not with the compound of formula I. Seizures were observed in all of the animals with all 3 compounds when dosed at 300 mg/kg. Additionally, at the 300 mg/kg oral dose resulted in 100 and 80% lethality for the compound of formula II and the racemate while no deaths were observed with the compound of formula I.

Administered i.p., all of the compounds produced seizures at 100 mg/kg. No deaths were observed with the compound of formula I whereas the compound of formula II and the racemate resulted in lethality of 100% and 20%, respectively. At the 300 mg/kg oral dose all of the lethality was observed for all of the compounds.

TABLE I

Effects on Uptake In Vitro

| Compound | IC50 (mM) | SEM |
| --- | --- | --- |
| [$^3$H]-Dopamine Uptake | | |
| Bupropion | 1.9 | 0.15 |
| Formula (I) | 9.3 | 0.41 |
| Formula (II) | >100 | |
| [3H]-Noradrenaline Uptake | | |
| Bupropion | 2.2 | 0.7 |
| Formula (I) | 1.1 | 0.07 |
| Formula (II) | >30 | |
| Imipramine | 0.072 | 0.020 |
| [$^3$H]-Serotonin Uptake | | |
| Bupropion | >30 | |
| Formula (I) | >30 | |
| Formula (II) | >100 | |
| Imipramine | 0.24 | 0.03 |

TABLE 2

Adverse Events Associated with Compounds of Formula I, Formula II and the Racemate

| Compound | Route | Dose (mg/kg) | Seizures (%) | Time to Seizures (min) | % Died | Time to Death (min) |
| --- | --- | --- | --- | --- | --- | --- |
| Formula I | i.p. | 100 | 100 | 3.93 | 0 | n/a |
| Formula I | p.o. | 100 | 0 | n/a | 0 | n/a |
| Formula I | i.p. | 300 | 100 | 3.95 | 100 | 6 |
| Formula I | p.o. | 300 | 100 | 11.23 | 0 | n/a |
| Formula II | i.p. | 100 | 20 | 5 | 100 | 7 |
| Formula II | p.o. | 100 | 100 | 7.2 | 0 | n/a |
| Formula II | i.p. | 300 | 100 | 1.1 | 100 | 6 |
| Formula II | p.o. | 300 | 100 | 6.8 | 100 | 7 |
| Racemate | i.p. | 100 | 100 | 3 | 20 | 14 |
| Racemate | p.o. | 100 | 100 | 9.2 | 0 | n/a |
| Racemate | i.p. | 300 | 100 | 3 | 100 | 3 |
| Racemate | p.o. | 300 | 100 | 6.8 | 80 | 7 |

N/a denotes that the effect was not observed and, therefore, no percentage was given.

What is claimed is:

1. A method for inhibiting noradrenaline uptake, dopamine uptake or both comprising the administration of (+)-(2S, 3S)-2-(3-chlorophenyl)-3,5,5-trimehtyl-2-morpholinol or pharmaceutically acceptable salts and solvates thereof.

* * * * *